United States Patent [19]

Bayless

[11] Patent Number: 5,344,583
[45] Date of Patent: Sep. 6, 1994

[54] COMPOSITION FOR REMOVING NAIL ENAMEL FROM ARTIFICIAL NAILS

[75] Inventor: Ronnie E. Bayless, Plant City, Fla.

[73] Assignee: Dotolo Research Corp., Largo, Fla.

[21] Appl. No.: 112,701

[22] Filed: Aug. 26, 1993

[51] Int. Cl.$^5$ .......................... C11D 3/18; C11D 3/20; C11D 1/83; C11D 9/36
[52] U.S. Cl. .................................... 252/171; 252/153; 252/162; 252/170; 252/542; 252/DIG. 8; 252/364; 252/39.7; 252/399; 252/549; 252/174.19; 252/544; 252/546; 252/174.15
[58] Field of Search ............... 252/153, 162, 170, 171, 252/542, DIG. 8, 364, 397, 399, 549, 174.19, 544, 546, 174.15; 134/29, 40

[56] References Cited

U.S. PATENT DOCUMENTS

| 3,686,701 | 8/1972 | Charle et al. | 252/364 X |
| 4,669,491 | 6/1987 | Weisberg et al. | 132/73 |
| 4,717,498 | 1/1988 | Maxon | 252/174.15 |
| 5,210,133 | 5/1993 | O'Lenick | 525/54.1 |

FOREIGN PATENT DOCUMENTS 1135710 5/1989 Japan.

Primary Examiner—Paul Lieberman
Assistant Examiner—Douglas McGinty
Attorney, Agent, or Firm—Marshall & Melhorn

[57] ABSTRACT

A non-aqueous composition for removing nail enamel from artificial nails, the composition containing d-limonene, methyl acetate cocamide DEA/dihexyl sodium sulfosuccinate and dimethicone copolyol.

3 Claims, No Drawings

COMPOSITION FOR REMOVING NAIL ENAMEL FROM ARTIFICIAL NAILS

The present invention relates to a composition and method for removing nail enamel from artificial nails, the composition comprising d-limonene, methyl acetate, cocamide DEA/dihexyl sodium sulfonate and dimithicone copolyol.

BACKGROUND OF THE INVENTION

In the past, compositions for removing nail enamel from artificial nails that removed the enamel speedily also damaged and sometimes destroyed the nails. Thus, it is desirable to provide a composition that removes the nail enamel speedily and effectively but does not cause unwanted damage to the nails.

OBJECTS OF THE INVENTION

It is an object of the invention to provide a composition for removing nail enamel from artificial nails, the composition being non-toxic, effective and safe, there being no unwanted damage to the nails.

It is an object of the present invention to provide a non-aqueous composition for removing nail enamel from artificial nails, the composition comprising the following ingredients in approximate percentage by weight:

| Ingredient | Percent by Weight |
| --- | --- |
| d-limonene | 30–42 |
| Methyl acetate | 52–66 |
| cocamide DEA/Dihexyl sodium sulfosuccinate | 1–5 |
| dimethicone copolyol | 0.2–3 |

These and other objects will be apparent from the specification that follows, and the appended claims.

SUMMARY OF THE INVENTION

The present invention provides:
1. A non-aqueous composition comprising
   (A) d-limonene;
   (B) methyl acetate;
   (C) about ½ to 8 percent by weight of the composition of cocamide DEA/dihexyl sodium sulfosuccinate; and
   (D) about 0.2 to 3 percent by weight of the composition of dimethicone copolyol, the amount of (A) and (B) being at least about 90 percent by weight of the composition.

The present invention also provides a method of removing nail enamel from artificial nails comprising the steps of applying the composition of to a nail enamel coating on an artificial nail, allowing the coated nail and composition to remain in contact for a time sufficient to loosen the coating from the nail; and separating the coating and the composition from the artificial nail.

DETAILED DESCRIPTION OF THE INVENTION

The non-aqueous compositions for removing nail enamel from artificial nails have the following ingredients in approximate percentage by weight:

| Ingredient | Percent by Weight | | |
| --- | --- | --- | --- |
| | Preferred | General | Optimum |
| d-limonene | 30–42 | 30–70 | 36 |
| methyl acetate | 52–66 | 30–70 | 60 |
| cocamide DEA/dihexyl sodium sulfosuccinate | 1–5 | 1/2–8 | 3 |
| dimethicone copolyol | 0.2–3 | 0.1–4 | 1 |

The methyl acetate is used to aid in the speedy removal of the nail enamel coating and, yet, does not destroy or do unwanted damage to the nails.

The surfactant and the dimethicone copolyol help balance the desirable properties of the non-toxic, yet effective nail enamel remover composition.

The dimethicone copolyol (CAS Numbers 64 365-23-F, 68937-54-2) is a polymer of dimethylsiloxame with polyethylene and or polyoxypropylene side chains. The material is specified as Abil 8842 TM by Goldschmidt.

The above described ingredients are easily mixed together and are compatible and miscible in the solvents d-limonene and methyl acetate. The mixed ingredients provide a superior nail removing composition that is safe, speedy, effective and reliable.

What is claimed is:

1. A non-aqueous composition for removing nail enamel from artificial nails, the composition comprising the following ingredients in approximate percentage by weight:

| Ingredient | Percent by Weight |
| --- | --- |
| d-limonene | 30–42 |
| Methyl acetate | 52–66 |
| cocamide DEA/Dihexyl sodium sulfosuccinate | 1/2–8 |
| dimethicone copolyol | 0.1–4 |

2. A nail enamel removing composition for removing enamel from artificial nails, the composition consisting of the following ingredients in approximate percent by weight:

| Ingredients | Percent by Weight |
| --- | --- |
| d-limonene | 30–70 |
| methyl acetate | 30–70 |
| cocamide DEA/dihexyl sodium sulfosuccinate | 1–5 |
| dimethicone copolyol | 0.2–3 |

3. A composition as defined in claim 1 having the following ingredients in approximate percentage by weight:

| Ingredients | Percent by Weight |
| --- | --- |
| d-limonene | 36 |
| methyl acetate | 60 |
| cocamide DEA/dihexyl | 3 |
| dimethicone copolyol | 1 |

* * * * *